(12) United States Patent
Teasley

(10) Patent No.: US 7,910,653 B2
(45) Date of Patent: *Mar. 22, 2011

(54) PROCESS FOR THE PREPARATION OF ARYLENE FLUORINATED SULFONIMIDE POLYMERS AND MEMBRANES

(75) Inventor: Mark F. Teasley, Landenberg, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 350 days.

This patent is subject to a terminal disclaimer.

(21) Appl. No.: 11/865,084

(22) Filed: Oct. 1, 2007

(65) Prior Publication Data

US 2008/0214732 A1    Sep. 4, 2008

Related U.S. Application Data

(60) Provisional application No. 60/849,430, filed on Oct. 4, 2006.

(51) Int. Cl.
*C08G 75/30*      (2006.01)
*H01M 8/10*      (2006.01)

(52) U.S. Cl. ............ 524/717; 524/701; 528/7; 528/377; 528/391; 549/4; 549/42; 549/46; 549/48

(58) Field of Classification Search .................. 524/717, 524/701; 429/12; 528/7, 377, 391; 549/4, 549/42, 46, 48

See application file for complete search history.

(56) References Cited

U.S. PATENT DOCUMENTS

| | | | |
|---|---|---|---|
| 3,664,915 A | 5/1972 | Gore | |
| 3,953,566 A | 4/1976 | Gore | |
| 3,962,153 A | 6/1976 | Gore | |
| 4,187,390 A | 2/1980 | Gore | |
| 5,547,551 A | 8/1996 | Bahar et al. | |
| 5,962,631 A | 10/1999 | Woo et al. | |
| 6,110,333 A | 8/2000 | Spethmann et al. | |
| 6,353,072 B1 | 3/2002 | Towns et al. | |
| 7,135,537 B2 | 11/2006 | Hofmann et al. | |
| 2008/0177088 A1 | 7/2008 | Teasley | |

FOREIGN PATENT DOCUMENTS

| WO | WO 97/28129 A1 | 8/1997 |
|---|---|---|
| WO | WO 00/53656 A1 | 9/2000 |
| WO | WO 2005/001979 A2 | 1/2005 |

OTHER PUBLICATIONS

Wang et al., Direct Polymerization of Sulfonated Poly(Arylene Ether Sulfone) Random (Statistical) Copolymers: Candidates for New Proton Exchange Membranes, Journal of Membrane Science, 2002, vol. 197:231-242.
Yamamoto, Electrically Conducting and Thermally Stable Conjugated Poly (Arylene)s Prepared by Organometallic Processes, Progress in Polymer Science, 1992, vol. 17:1153-1205.
Ioyda et al., Homocoupling of Aryl Halides Using Nickel (II) Complex and Zinc in the Presence of Et4NI. An Efficient Method for the Synthesis of Biaryls and Bipyridines, Bullentin of the Chemical Society of Japan, 1990, vol. 63:80.
Colon et al., High Molecular Weight Aromatic Polymers by Nickel Coupling of Aryl Polychlorides, Journal of Polymer Science, Part A, Polymer Chemistry Edition, 1990, vol. 28:367.
Miyaura et al., The Palladium-Catalyzed Cross-Coupling Reaction of Phenylboronic Acid With Haloarenes in the Presence of Bases, Synthetic Communication, 1981, vol. 11:513.
Wallow et al., Palladium-Mediated Poly(p-phenylene) Synthesis: Evidence for a Molecular Weight Limiting Phosphine Arylation Reaction, American Chemical Society, Polymer Preprint, 1993, vol. 34:1009.
H. Gilman et al., Relative Reactivities of Organometallic Compounds. XVIII. Selective Metalations of Dibenzothiophene, Journal of Organic Chemistry, 1938, vol. 3:120-124.
Gilman et al., Some Brominated Dibenzothiophene Derivatives, J. Am. Chem. Soc., 1953, vol. 75:3843-3845.

*Primary Examiner* — Kelechi C Egwim

(57) ABSTRACT

Aromatic sulfonimide ionene polymers useful as membranes in electrochemical cells are prepared.

22 Claims, No Drawings

PROCESS FOR THE PREPARATION OF ARYLENE FLUORINATED SULFONIMIDE POLYMERS AND MEMBRANES

This invention was made with government support under Contract No. DE-FC04-02AL67606 awarded by the U.S. Department of Energy. The government has certain rights in the invention.

FIELD OF INVENTION

Described herein is the preparation of aromatic sulfonimide polymers useful as membranes in electrochemical cells.

BACKGROUND

Polymer electrolyte membrane fuel cells (PEMFC) are expected to provide higher efficiencies, fewer environmental pollutants, and reduced operating and maintenance costs than traditional power sources. An important component of a PEMFC is a polymer electrolyte membrane (PEM). The range of potential candidates for use as membrane materials in PEMFCs is limited by a number of requirements, including chemical, thermal, and mechanical stability, high ionic conductivity, and low reactant permeability. Developments have been made in the use of sulfonic acid functionalized polymers, including membranes such as Nafion® perfluorosulfonic acid membranes.

Known membranes made from sulfonic acid functionalized polymers have been found to have inadequate performance at temperatures greater than 100° C. due, in part, to the dependence of the membranes on water for proton conduction. Above 100° C., pressure constraints limit the amount of water that can be used to hydrate a membrane. At relatively low levels of humidity, insufficient water is present within the membrane to support the transport of protons. In addition to improved performance at higher temperatures, it is also desirable to have improved mechanical stability at such temperatures.

Alternatives to perfluorosulfonic acid membranes include membranes based on aromatic engineering polymers. For example, poly(arylene ether)s, poly(arylene ether ketone)s, and poly(arylene ether sulfone)s are engineering polymers known for their chemical, thermal, and mechanical stability. Poly(arylene ether)s, poly(arylene ether ketone)s, and poly(arylene ether sulfone)s can be sulfonated to produce sulfonic-acid functionalized aromatic polymers. However, due to relatively poor control inherent in the process, post-polymerization sulfonation can result in sulfonation on the most electron-rich aromatic rings, essentially those substituted with just the ether functional groups, which are also the most activated to a subsequent thermal decomposition of the sulfonic acid groups.

Another method for producing sulfonic-acid functionalized aromatic polymers is by polymerizing sulfonated monomers, as disclosed, for example, by F. Wang et al., "Direct polymerization of sulfonated poly(arylene ether sulfone) random (statistical) copolymers: candidates for new proton exchange membranes", Journal of Membrane Science, Vol. 197 (1-2), pp. 231-242 (2002). This allows the sulfonic acid groups to be located on the most electron-deficient aromatic rings to improve their thermal stability. However, the proton conductivity of sulfonated aromatic polymers made by either of the two methods discussed hereinabove is limited by the acid strength of the aromatic sulfonic acid groups, especially at low relative humidity.

The use of fluorosulfonimide functional groups instead of sulfonic acid groups at similar equivalent weights can increase the proton conductivity of the resulting aromatic polymers because fluorosulfonimides possess higher acid strengths. M. Hofmann (U.S. Pat. No. 7,135,537) prepared aromatic polymers containing fluorosulfonimide functionalities in the backbone. However, all the polymers prepared also contained an ether functionality in the aromatic backbone, which decreases their stability. The higher acid strength of the fluorosulfonimide groups leads to thermal and chemical instability in the ether groups relative to comparable sulfonated aromatic polymers, and the flexibility of the ether groups increases the potential for excessive water uptake, which reduces their mechanical stability. In addition, electron-rich aromatic rings substituted with ether groups are more susceptible to chemical degradation under the oxidative conditions inherent in PEMFC, which are due, in part, to high permeability to the fuel cell reactants.

A need remains for a process to prepare polymers for membranes in applications such as fuel cells that exhibit good ionic conductivity, hydration, chemical, thermal, and mechanical stability at high temperatures, and low reactant permeability.

SUMMARY

Described herein is a process for making a polymer comprising polymerizing a compound of Formula (I):

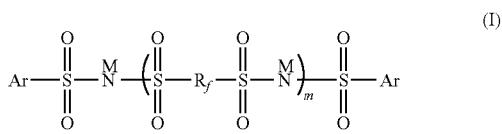

wherein Ar is a univalent group of Formula (II), (III), or (IV):

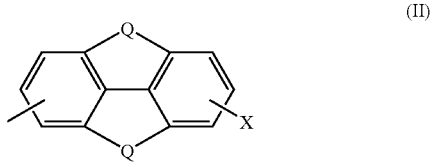

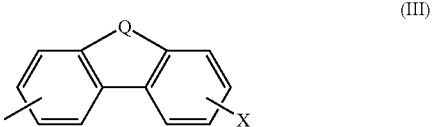

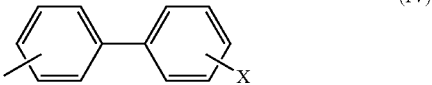

and is optionally substituted with one or more fluorine; $R_f$ is a straight chain, branched or cyclic, perfluorinated alkylene group having from 1 to 20 carbon atoms and optionally substituted with one or more ether oxygens or halogens; m is 1-6; p indicates the average number of monomeric units; M is one or more of monovalent cation; Q is S, $SO_2$, CO, or $CR^1R^2$, wherein $R^1$ and $R^2$ are independently branched or cyclic perfluorinated alkyl groups having 1 to 10 carbon atoms, and wherein $R^1$ and $R^2$ can together form a ring; and X is chlorine, bromine, iodine, methanesulfonate, or trifluoromethanesulfonate; wherein the polymerization is performed in the presence of a zerovalent transition metal and a neutral ligand.

Also described here is a process wherein a copolymer is formed by polymerizing a compound of Formula (I) and a compound of Formula (IX):

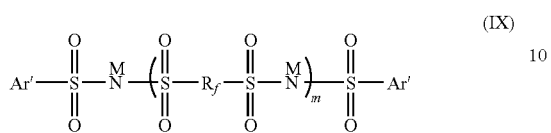

(IX)

wherein Ar' is a univalent group of Formula (X), (XI), or (XII):

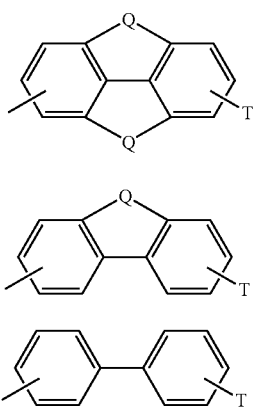

(X)

(XI)

(XII)

wherein T is a boronic acid group, a boronic ester group or a borane group.

Also described herein is a polymer made by the disclosed processes.

DETAILED DESCRIPTION

Disclosed herein are processes to prepare polymers that are useful as cation-exchange resins. The cation-exchange resins are useful in making proton-exchange membranes for electrochemical cells such as fuel cells and can be used in any application wherein cation-exchange capacity is desired. The polymers described herein can be either homopolymers or copolymers.

The process comprises polymerizing a compound of Formula (I):

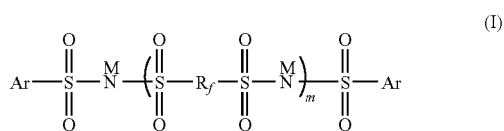

(I)

wherein Ar is a univalent group of Formula (II), (III), or (IV):

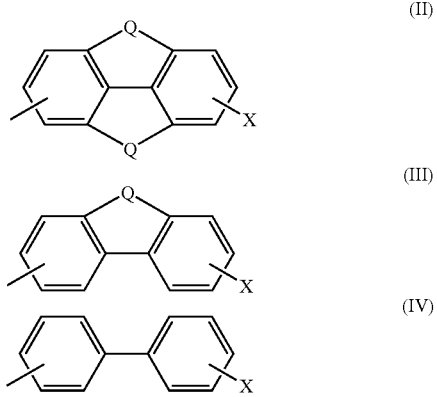

(II)

(III)

(IV)

and is optionally substituted with one or more fluorine;

$R_f$ is a straight chain, branched or cyclic, perfluorinated alkylene group having from 1 to 20 carbon atoms and optionally substituted with one or more ether oxygens or halogens;

m is 1-6;

p indicates the average number of monomeric units

M is one or more of monovalent cation;

Q is S, $SO_2$, CO, or $CR^1R^2$, wherein $R^1$ and $R^2$ are independently branched or cyclic perfluorinated alkyl groups having 1 to 10 carbon atoms, and wherein $R^1$ and $R^2$ can together form a ring; and X is chlorine, bromine, iodine, methanesulfonate, or trifluoromethanesulfonate;

wherein the polymerization is performed in the presence of a zerovalent transition metal compound and a neutral ligand.

Ar is attached at any open valence of the ring as indicated.

X is chlorine, bromine, iodine, methanesulfonate, or trifluoromethanesulfonate, and can be attached to any open valence in the indicated ring of Ar. In one embodiment, X is chlorine or bromine.

The monovalent cation M can be a single cation or a mixture of different cations. In one embodiment, the M is K, Na, Li, or H.

By "perfluorinated alkylene" it is meant a divalent group containing carbon and fluorine connected by single bonds, optionally substituted with ether oxygens or other halogens, and containing two free valences to different carbon atoms. It can be linear, branched, or cyclic. In one embodiment $R_f$ is a perfluorinated alkylene group having from 2 to 10, or 2 to 4, carbon atoms.

The term "copolymer" is intended to include oligomers and copolymers having two or more different repeating units. A copolymer having repeating units derived from a first monomer "X-A-X" and a second monomer "X-B-X" will have repeating units (-A-) and (-B-). The copolymers described herein can be random or block copolymers.

The practical upper limit to the number of monomeric units in the polymer is determined in part by the desired solubility of a polymer in a particular solvent or class of solvents. As the total number of monomeric units increases, the molecular weight of the polymer increases. The increase in molecular weight is generally expected to result in a reduced solubility of the polymer in a particular solvent. Moreover, in one embodiment, the number of monomeric units at which a polymer becomes substantially insoluble in a given solvent is dependent in part upon the structure of the monomer. In one embodiment, the number of monomeric units at which a copolymer becomes substantially insoluble in a given solvent is dependent in part upon the ratio of the comonomers. For example, a polymer composed of flexible monomers may become substantially insoluble in an organic solvent if the resulting polymer becomes too rigid in the course of polymerization. As another example, a copolymer composed of several monomers may become substantially insoluble in an organic solvent when ratio of rigid monomeric units to flexible monomeric units is too large. The selection of polymer molecular weight, polymer and copolymer composition, and a solvent is within the purview of one skilled in the art.

In one embodiment, Ar is a univalent group of Formula (VI), (VII), or (VIII):

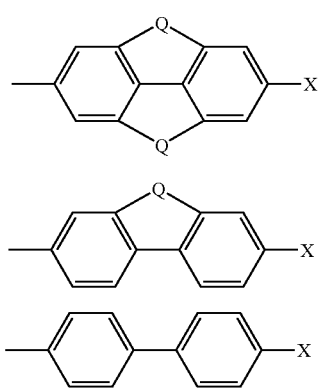

wherein Ar is connected to Formula (I) at the indicated position. In another embodiment, Ar is Formula (VII) or (VIII).

In another embodiment the process comprises the polymerization of a compound of Formula (I) and a compound of Formula (IX):

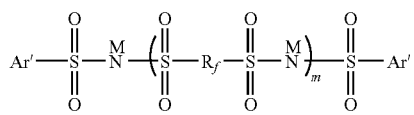

to form a copolymer wherein Ar' is a univalent group of Formula (X), (XI), or (XIII):

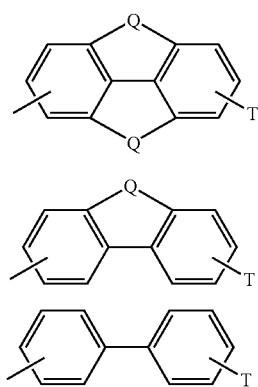

wherein T is a boronic acid group, a boronic ester group or a borane group.

The compositions of Formula (I), used as monomers in the process described herein, and the reactants used to prepare them, may be obtained commercially or be prepared using any known method in the art or disclosed herein. One suitable method to synthesize the compositions of Formula (I) is to react a fluorinated disulfonamide with two equivalents of a compound comprising the desired arylene with a halogen substituent and a sulfonyl halide substituent. One method to prepare the disulfonamide is described in PCT Appl. 2005/001979, Example 1. One method to prepare the arylene compound is described in PCT Appl. 1997/28129, Example 4. Methods to synthesis the monomers and the reactants are also disclosed in co-owned and concurrently filed U.S. Applications docket number CL3657 and CL3669.

The polymerizations as described herein can generally be performed by synthetic routes in which the chlorine, bromine, iodine, methanesulfonate, or trifluoromethanesulfonate leaving groups of the monomers are eliminated in carbon-carbon bond-forming reactions. Such carbon-carbon bond-forming reactions are typically mediated by a zerovalent transition metal compound that contains neutral ligands. In one embodiment, the zerovalent transition metal compound contains nickel or palladium.

The compositions of Formula (I) may also be reacted to form larger monomeric units that are then polymerized alone or with other monomers to form the polymers disclosed herein. For example, a copolymer $(-A-)_x(-B-)_y$ may be formed by copolymerizing monomer X-A-X with monomer X-B-X, or by forming larger monomer X-A-B-X and polymerizing that monomer. In both cases, the resulting polymer is considered a copolymer derived from monomer X-A-X and monomer X-B-X.

Neutral ligands are defined as ligands that are neutral, with respect to charge, when formally removed from the metal in their closed shell electronic state. Neutral ligands contain at least one lone pair of electrons, a pi-bond, or a sigma bond that is capable of binding to the transition metal. For the processes described herein, the neutral ligand may also be a combination of two or more neutral ligands. Neutral ligands may also be polydentate when more than one neutral ligand is connected via a bond or a hydrocarbyl, substituted hydrocarbyl or a functional group tether. A neutral ligand may be a substituent of another metal complex, either the same or different, such that multiple complexes are bound together. Neutral ligands can include carbonyls, thiocarbonyls, carbenes, carbynes, allyls, alkenes, olefins, cyanides, nitriles, carbon monoxide, phosphorus containing compounds such as phosphides, phosphines, or phosphites, acetonitrile, tetrahydrofuran, tertiary amines (including heterocyclic amines), ethers, esters, phosphates, phosphine oxides, and amine oxides.

Three synthetic methods based on zerovalent transition metal compounds that can be used to prepare the polymers are described herein. In each method, the zerovalent transition metal compound that is the active species in carbon-carbon bond formation can be introduced directly into the reaction, or can be generated in situ under the reaction conditions from a precursor transition metal compound and one or more neutral ligands.

In a first synthetic method, as described in Yamamoto, Progress in Polymer Science, Vol. 17, p 1153 (1992), the dihalo derivatives of the monomers are reacted with stoichiometric amounts of a zerovalent nickel compound, such as a coordination compound like bis(1,5-cyclooctadiene)nickel (0), and a neutral ligand, such as triphenylphosphine or 2,2'-bipyridine. These components react to generate the zerovalent nickel compound that is the active species in the polymerization reaction. A second neutral ligand, such as 1,5-cyclooctadiene, can be used to stabilize the active zerovalent nickel compound.

In a second synthetic method, as described in U.S. Pat. No. 5,962,631, Ioyda et al., Bulletin of the Chemical Society of Japan, Vol. 63, p. 80 (1990), and Colon et al., Journal of Polymer Science, Part A, Polymer Chemistry Edition, Vol. 28, p. 367 (1990), the dihalo derivatives of the monomers are reacted with catalytic amounts of a divalent nickel compound in the presence of one or more neutral ligands in the presence of stoichiometric amounts of a material capable of reducing the divalent nickel ion to zerovalent nickel.

In the second synthetic method, the catalyst is formed from a divalent nickel salt. The nickel salt may be any nickel salt that can be converted to the zerovalent state under reaction conditions. Suitable nickel salts are the nickel halides, typically nickel dichloride or nickel dibromide, or coordination compounds, typically bis(triphenylphosphine)nickel dichloride or (2,2'-bipyridine)nickel dichloride. The divalent nickel salt is typically present in an amount of about 0.01 mole percent or greater, more typically about 0.1 mole percent or greater or 1.0 mole percent or greater. The amount of divalent nickel salt present is typically about 30 mole percent or less, more typically about 15 mole percent or less based on the amount of monomers present.

In the second synthetic method, the polymerization is performed in the presence of a material capable of reducing the divalent nickel ion to the zerovalent state. Suitable material includes any metal that is more easily oxidized than nickel. Suitable metals include zinc, magnesium, calcium and lithium, with zinc in the powder form being typical. At least stoichiometric amounts of reducing agent based on the monomers are required to maintain the nickel species in the zerovalent state throughout the reaction. Typically, about 150 mole percent or greater, more typically about 200 mole percent or greater, or about 250 mole percent or greater is used. The reducing agent is typically present in an amount of about 500 mole percent or less, about 400 mole percent or less, or about 300 mole percent or less based on the amount of monomer.

Also present in the second synthetic method are one or more compounds capable of acting as a ligand. Suitable ligands are neutral ligands as described above, and include trihydrocarbylphosphines. Typical ligands are monodentate, such as triaryl or trialkylphosphines like triphenylphosphine, or bidentate, such as 2,2'-bipyridine. A compound capable of acting as a monodentate ligand is typically present in an amount of from about 10 mole percent or greater, or about 20 mole percent or greater based on the monomer. A compound capable of acting as a monodentate ligand is typically present in an amount of about 100 mole percent or less, about 50 mole percent or less, or about 40 mole percent or less. A compound capable of acting as a bidentate ligand is typically present in an amount that is about a molar equivalent or greater based on the divalent nickel salt. Alternatively, the bidentate ligand can be incorporated into the nickel salt as a coordination compound as described above.

In a third synthetic method, as described in PCT application WO 00/53656 and U.S. Pat. No. 6,353,072, a dihalo derivative of one monomer is reacted with a derivative of another monomer having two leaving groups selected from boronic acid (—$B(OH)_2$) or boronate salt, boronic acid esters (—$BOR_2$) or (—$B(ORO)$)), and boranes (—$BR_2$), where R is generally a hydrocarbyl group, in the presence of a catalytic amount of a zerovalent palladium compound containing a neutral ligand as described above, such as tetrakis(triphenylphosphine)palladium(0). If the leaving group is a boronic ester or borane group, the reaction mixture should include sufficient water or an organic base to hydrolyze the boronic ester or borane group to the corresponding boronic acid group. The diboronic derivative of a monomer can be prepared from the dihalo derivative by known methods, such as those described in Miyaura et al., Synthetic Communication, Vol. 11, p. 513 (1981) and Wallow et al., American Chemical Society, Polymer Preprint, Vol. 34, (1), p. 1009 (1993).

All of the synthetic methods discussed herein can be performed in the presence of a compound capable of accelerating the reaction. Suitable accelerators include alkali metal halides such as sodium bromide, potassium bromide, sodium iodide, tetraethylammonium iodide, and potassium iodide. The accelerator is used in a sufficient amount to accelerate the reaction, typically 10 mole percent to 100 mole percent based on the monomer.

The reactions are typically run in a suitable solvent or mixture of solvents, that is a solvent that is not detrimental to catalyst, reactant and product, and preferably one is which the reactants and products are soluble. Suitable solvents include N,N-dimethylformamide (DMF), toluene, tetrahydrofuran (THF), acetone, anisole, acetonitrile, N,N-dimethylacetamide (DMAc), and N-methylpyrrolidinone (NMP). The amount of solvent used in this process can vary over a wide range. Generally, it is desired to use as little solvent as possible. The reactions are typically conducted in the absence of oxygen and moisture, as the presence of oxygen can be detrimental to the catalyst and the presence of a significant amount of water could lead to premature termination of the process. More typically, the reaction is performed under an inert atmosphere such as nitrogen or argon.

The reactions can be performed at any temperature at which the reaction proceeds at a reasonable rate and does not lead to degradation of the product or catalyst. Generally, the reaction is performed at a temperature of about 20° C. to about 200° C., more typically less than 100° C. The reaction time is dependent upon the reaction temperature, the amount of catalyst and the concentration of the reactants, and is usually about 1 hour to about 100 hours.

The polymers prepared by the disclosed methods can be recovered according to conventional techniques including filtration and precipitation using a non-solvent. They also can be dissolved or dispersed in a suitable solvent for further processing.

The polymers described herein can be formed into membranes using any conventional method such as but not limited to solution or dispersion film casting or extrusion techniques. The membrane thickness can be varied as desired for a particular application. Typically, for electrochemical uses, the membrane thickness is less than about 350 μm, more typically in the range of about 25 μm to about 175 μm. If desired, the membrane can be a laminate of two different polymers such as two polymers having different equivalent weight or other properties. Such films can be made by laminating two membranes. Alternatively, one or both of the laminate components can be cast from solution or dispersion. When the membrane is a laminate, the chemical identities of the monomer units in the additional polymer can independently be the same as or different from the identities of the analogous monomer units of the first polymer. One of ordinary skill in the art will understand that membranes prepared from the dispersions may have utility in packaging, in non-electrochemical membrane applications, as an adhesive or other functional layer in a multi-layer film or sheet structure, and other classic applications for polymer films and sheets that are outside the field of electrochemistry. For the purposes of the present invention, the term "membrane", a term of art in common use in electrochemistry, is synonymous with the terms "film" or "sheet", which are terms of art in more general usage, but refer to the same articles.

The membrane may optionally include a porous support or reinforcement for the purposes of improving mechanical properties, for decreasing cost and/or other reasons. The porous support may be made from a wide range of materials, such as but not limited to non-woven or woven fabrics, using various weaves such as the plain weave, basket weave, leno weave, or others. The porous support may be made from glass, hydrocarbon polymers such as polyolefins, (e.g., polyethylene, polypropylene, polybutylene, and copolymers), and perhalogenated polymers such as polychlorotrifluoroethylene. Porous inorganic or ceramic materials may also be used. For resistance to thermal and chemical degradation, the support typically is made from a fluoropolymer, more typically a perfluoropolymer. For example, the perfluoropolymer of the porous support can be a microporous film of polytetrafluoroethylene (PTFE) or a copolymer of tetrafluoroethylene. Microporous PTFE films and sheeting are known that are suitable for use as a support layer. For example, U.S. Pat. No. 3,664,915 discloses uniaxially stretched film having at least 40% voids. U.S. Pat. Nos. 3,953,566, 3,962,153 and 4,187,390 disclose porous PTFE films having at least 70% voids. Impregnation of expanded PTFE (ePTFE) with perfluorinated sulfonic acid polymer is disclosed in U.S. Pat. Nos. 5,547,551 and 6,110,333. ePTFE is available under the trade name "Goretex" from W. L. Gore and Associates, Inc., Elkton, Md., and under the trade name "Tetratex" from Tetratec, Feasterville, Pa.

Membrane electrode assemblies (MEA) and fuel cells therefrom are well known in the art and can comprise any of the membranes described above. One suitable embodiment is described herein. An ionomeric polymer membrane is used to form a MEA by combining it with a catalyst layer, comprising a catalyst such as platinum, which is unsupported or supported on carbon particles, a binder such as Nafion®, and a gas diffusion backing. The catalyst layers may be made from well-known electrically conductive, catalytically active particles or materials and may be made by methods well known in the art. The catalyst layer may be formed as a film of a polymer that serves as a binder for the catalyst particles. The binder polymer can be a hydrophobic polymer, a hydrophilic polymer, or a mixture of such polymers. The binder polymer is typically ionomeric and can be the same ionomer as in the membrane. A fuel cell is constructed from a single MEA or multiple MEAs stacked in series by further providing porous and electrically conductive anode and cathode gas diffusion backings, gaskets for sealing the edge of the MEA(s), which also provide an electrically insulating layer, graphite current collector blocks with flow fields for gas distribution, aluminum end blocks with tie rods to hold the fuel cell together, an anode inlet and outlet for fuel such as hydrogen, and a cathode gas inlet and outlet for oxidant such as air.

EXAMPLES

The present invention is further defined in the following Examples. It should be understood that these Examples, while indicating preferred embodiments of the invention, are given by way of illustration only.
Materials and Methods Anhydrous solvents were used for all synthetic reactions unless they were to be used in combination with water. Reagent-grade solvents were used for purifications and aqueous reactions. Synthetic reactions that were performed under anhydrous conditions were assembled in a glove box, which was purged with dry nitrogen, as described in the relevant Examples.

ABBREVIATIONS

DMSO dimethylsulfoxide
NMR nuclear magnetic resonance

Octafluorobutane-1,4-Disulfonamide

This compound was synthesized according to the procedure of M. F. Teasley, Z.-Y. Yang, WO2005001979 A2, Jan. 6, 2005, Example 1.

A 1 L 3N Morton flask equipped with a glass mechanical stirrer, 125 mL addition funnel with gas outlet, and gas dispersion tube was purged with nitrogen while adding sodium hydrosulfite (100 g, 0.49 mol), sodium bicarbonate (55 g, 0.66 mol), acetonitrile (150 mL), and water (150 mL). The addition funnel was charged with 1,4-diiodo-octafluorobutane (100 g, 0.22 mol). The solution was deoxygenated with nitrogen for 1 hour. The diiodide was added dropwise at a sufficient rate to observe rapid gas evolution. The mixture was stirred an additional 30 minutes. $^{19}$F NMR (D$_2$O) indicated complete reaction to give octafluorobutane-1,4-disulfinate, disodium salt: −122.71 (m, —CF$_2$—CF$_2$—), −130.35 (m, 2 —CF$_2$—SO$_2$Na).

The solvents were evaporated in a 1 L RBF. The residue was dissolved in water (500 mL) and returned to the reaction flask substituting a thermocouple for the addition funnel. The solution was deoxygenated with nitrogen and cooled to <−5° C. Chlorine was bubbled through the solution at a rate to maintain the temperature between −5 and 0° C. The reaction was monitored as it changed in color from pale yellow to dark purple to the final mustard yellow of the completed reaction. The mixture was extracted with dichloromethane (5×150 mL) to dissolve the solid yellow product. The organic phase was extracted once with water, dried with magnesium sulfate, and evaporated in a 1 L round-bottom flask at 40° C. The product was dried overnight in a cool vacuum oven under nitrogen purge to give 75.6 g (86.0% yield) of octafluorobutane-1,4-disulfonyl dichloride. $^{19}$F NMR (CDCl$_3$): −104.7 (m, 2 —CF$_2$—SO$_2$Cl), −119.3 (m, —CF$_2$—CF$_2$—).

The flask was transferred to the glove box and charged with potassium fluoride (55 g, 0.95 mol, 5 equiv.) and acetonitrile (200 mL). The flask was stirred overnight under nitrogen. The solution was poured into water (1 L) and swirled to separate the product as a heavy liquid, which was drained into a distillation flask. The product was distilled from phosphorus pentoxide using a 24-inch spinning band distillation column. A pure cut of 48.1 g (69% yield) of octafluorobutane-1,4-disulfonyl difluoride was obtained at 129.3-130.6° C. $^{19}$F NMR (CD$_3$CN): −120.55 (m, —CF$_2$—CF$_2$—), −108.49 (m, 2 —CF$_2$—SO$_2$—), 45.83 (t, 2 —SO$_2$F).

A 200 mL 2N round-bottom flask equipped with a stirring bar, septum, and dry ice condenser was purged with nitrogen and cooled in a dry ice bath. Liquid ammonia (10 mL) was condensed into the flask. Inside the glove box, a solution of octafluorobutane-1,4-disulfonyl difluoride (10.98 g, 30 mmol) in acetonitrile (50 mL) was prepared in a 100 mL Erlenmeyer flask and sealed with a septum. The solution was added dropwise by cannula to the liquid ammonia and stirred for 1 hour before warming to room temperature and stirring overnight. The mixture was poured into water (100 mL), acidified to pH 3, and extracted with ether (4×50 mL). The organic extracts were dried with MgSO$_4$, filtered, evaporated, and dried under vacuum to give 10.4 g. The product was vacuum sublimed at 170° C. and 90 mTorr to give 9.63 g (89% yield) of octafluorobutane-1,4-disulfonamide. $^{19}$F NMR (CD$_3$CN): −121.1 (m, —CF$_2$—CF$_2$—), −114.5 (m, 2 —CF$_2$—SO$_2$—NH$_2$).

4'-Bromo-Biphenyl-4-Sulfonyl Chloride

This compound was synthesized according to the procedure of M. J. Smithers, J. Preston, A. Stocker, WO9728129A1, Aug. 7, 1997, Example 4.

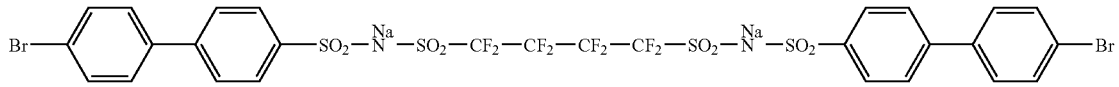

A 500 mL round-bottom-flask equipped with an addition funnel, stirring bar, and gas inlet was charged with 4-bromo-biphenyl (50 g, 0.215 mol) and chloroform (200 mL) then purged with nitrogen. Chlorosulfonic acid (18 mL, 0.27 mol) was added dropwise to the solution from the addition funnel then stirred for 1 hour. The resulting precipitate was collected by vacuum filtration, washed with cold chloroform, and dried under vacuum to give 61.97 g of 4'-bromo-biphenyl-4-sulfonic acid (92% yield).

A 500 mL round-bottom-flask equipped with an addition funnel, stirring bar, and gas inlet was charged with the 4-bromo-biphenyl sulfonic acid, DMF (200 mL) then purged with nitrogen. The flask was chilled in an ice-bath and thionyl chloride (45 mL, 0.62 mol) was added dropwise to the solution from the addition funnel. The flask was allowed to warm to room temperature and stirred for 3 hours. The solution was poured into 2 L ice water to precipitate the product, which was collected by vacuum filtration. The solids were dissolved in ether and the solution was dried with magnesium sulfate, filtered, and evaporated on a rotary evaporator. The resulting solids were dried under vacuum to give 59.66 g (84% yield) and recrystallized from hot toluene (100 mL) by adding cyclohexane (250 mL). The crystals were collected, washed with cyclohexane, and dried under vacuum to give 55.20 g of 4'-bromo-biphenyl-4-sulfonyl chloride (78% yield).

Example 1

Inside the glove box, a 100 mL round-bottom flask equipped with a reflux condenser, stirring bar, and septum was charged with 4'-bromo-biphenyl-4-sulfonyl chloride (6.63 g, 20 mmol), octafluorobutane-1,4-disulfonamide (3.60 g, 10 mmol), and acetonitrile (40 mL). Triethylamine (6 mL, 40 mmol) was added slowly by syringe. The solution was heated to a reflux overnight. The solution was cooled to room temperature, poured into an aqueous solution (150 mL) of 20% sodium hydroxide, and chilled in an ice bath to induce precipitation. The precipitate was collected by vacuum filtration dried under vacuum to give 9.86 g (99% yield). The solids were recrystallized by dissolving in water at a reflux, treating with decolorizing carbon, filtering the solution, and concentrating the solution at a reflux to 200 mL to induce crystallization. The white crystals were collected by vacuum filtration, washed with water, and dried overnight in a vacuum oven at 100° C. followed by 170° C. under a nitrogen purge to give 8.80 g (89% yield) of N,N'-bis(4'-bromo-biphenyl-4-sulfonyl)-octafluorobutane-1,4-disulfonamide, disodium salt, shown below. $^1$H NMR (DMSO-d$_6$): 7.67 (bm, 4H), 7.78 (d, J=8 Hz, 2H), 7.84 (d, J=8 Hz, 2H). $^{19}$F NMR (DMSO-d$_6$): −120.36 (m, —CF$_2$—CF$_2$—), −113.06 (m, 2 —CF$_2$—SO$_2$—).

Example 2

Inside the glove box, a 25 mL round-bottom flask equipped with a stirring bar and a septum was charged with bis(1,5-cyclooctadiene)nickel(0) (1.67 g, 6.06 mmol), 1,5-cyclooctadiene (0.656 g, 6.06 mmol), 2,2'-bipyridine (0.947 g, 6.06 mmol), and DMF (10 mL). The flask was heated to 60° C. under nitrogen for 30 minutes to give a dark violet-colored solution. Inside the glove box, a 25 mL round-bottom flask equipped with a septum was charged with N,N'-bis(4'-bromo-biphenyl-4-sulfonyl)-octafluorobutane-1,4-disulfonamide, disodium salt (3.00 g, 3.0 mmol) and DMF (10 mL). This solution was added by cannula to the reaction flask under nitrogen and maintained at 60° C. overnight. The gelatinous reaction mixture was poured into a 1:1 solution of hydrochloric acid and methanol to precipitate the solid polymer. The mixture was chopped in a blender to disperse the polymer into particles. The polymer was collected by vacuum filtration, washed with a 1:2 solution of hydrochloric acid and methanol followed by cold water, and dried in the vacuum oven at 70° C. under nitrogen purge to give 2.03 g (86% yield) of poly(p-quaterphenylene-sulfonimide-1,4-octafluorobutane-sulfonimide), shown below. $^1$H NMR (DMSO-d$_6$): 7.87 (bs). $^{19}$F NMR (DMSO-d$_6$): −120.33 (m, —CF$_2$—CF$_2$—), −112.97 (m, 2 —CF$_2$—SO$_2$—).

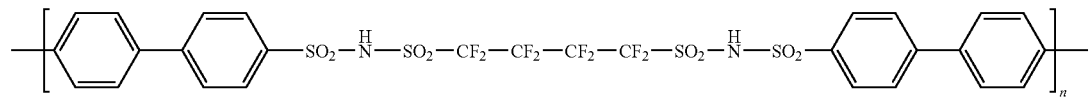

The polymer was redissolved in DMSO, filtered to remove insoluble particles, and re-precipitated by pouring into concentrated hydrochloric acid. The polymer was collected by vacuum filtration, washed with water, and dried overnight in the vacuum oven to give 1.63 g of polymer (69% yield). $\eta_{inh}$ (0.5 g/dL DMSO) 4.34 dL/g. The molecular weight distribution was measured by gel permeation chromatography in DMAc: $M_n$ 25,000, $M_w$ 121,000, $M_z$ 409,000. Thermo-gravimetric analysis (10° C./min scan rate) showed an onset of decomposition at 228° C. under nitrogen.

The polymer was dissolved in DMSO (10 mL) and filtered through a glass microfiber syringe filter into a smooth flat-bottom polymethylpentene Petri dish (nominal 10 cm diameter). The dish was placed on a level drying stage in an 80° C. vacuum oven under nitrogen purge. The dried membrane weighed 1.24 g. The membrane was freed by soaking in deionized water and redried in the vacuum oven. The membrane was tough and weighed 1.17 g.

Example 3

Inside the glove box, a 200 mL round-bottom flask equipped with a reflux condenser, stirring bar, and septum was charged with 4'-bromo-biphenyl-4-sulfonyl chloride (8.36 g, 25.3 mmol), octafluorobutane-1,4-disulfonamide (4.550 g, 12.6 mmol), and acetonitrile (80 mL). Triethylamine (7.6 mL, 54.3 mmol) was added slowly by syringe to give a mild exotherm. The solution was heated to a reflux overnight. The solution was cooled to room temperature and poured into an aqueous solution of sodium hydroxide (4 g, 0.1 mol) in water (200 mL) in a 1 L round-bottom flask. The solvents were evaporated on a rotary evaporator and the solids were dried under vacuum. The solids were recrystallized by dissolving in water (300 mL) at a reflux, filtering the solution, and concentrating the solution at a reflux to induce crystallization. The white crystals were collected by vacuum filtration, washed with water, and dried overnight in a vacuum oven at 150° C. under a nitrogen purge to give 11.24 g (89% yield) of N,N'-bis(4'-bromo-biphenyl-4-sulfonyl)-octafluorobutane-1,4-disulfonamide, disodium salt.

Example 4

Inside the glove box, a 100 mL round-bottom flask equipped with a stirring bar and a septum was charged with bis(1,5-cyclooctadiene)nickel(0) (3.06 g, 11.11 mmol), 1,5-cyclooctadiene (1.20 g, 11.11 mmol), 2,2'-bipyridine (1.74 g, 11.11 mmol), and DMF (20 mL). The flask was heated to 60° C. under nitrogen for 30 minutes to give a dark violet-colored solution. Inside the glove box, a 100 mL round-bottom flask equipped with a septum was charged with N,N'-bis(4'-bromo-biphenyl-4-sulfonyl)-octafluorobutane-1,4-disulfonamide, disodium salt (5.47 g, 5.5 mmol) and DMF (20 mL). This solution was added by cannula to the reaction flask under nitrogen and maintained at 60° C. overnight. The reaction mixture was poured into a 1:1 solution of hydrochloric acid and methanol to precipitate the solid polymer. The mixture was chopped in a blender to disperse the polymer into particles. The polymer was collected by vacuum filtration then dissolved in DMF and precipitated by pouring into a 1:1 solution of hydrochloric acid and methanol. The polymer was collected by vacuum filtration and dried in the vacuum oven at 70° C. under nitrogen purge to give 4.34 g (100% yield) of poly(p-quaterphenylene-sulfonimide-1,4-octafluorobutane-sulfonimide). $^1$H NMR (DMSO-d$_6$): 7.88 (bs). $^{19}$F NMR (DMSO-d$_6$): −120.34 (m, —CF$_2$—CF$_2$—), −113.00 (m, 2 —CF$_2$—SO$_2$—). $\eta_{inh}$ (0.5 g/dL DMSO) 3.52 dL/g. Gel permeation chromatography in DMAc showed a bimodal molecular weight distribution with a high molecular weight peak: $M_n$ 47,100, $M_w$ 124,000, $M_z$ 317,000.

The polymer was dissolved in DMF (80 mL) with heating to 50° C. The solution was filtered through a glass microfiber filter fitted to a stainless steel filter body using nitrogen pressure and collected in a plastic bottle. Sufficient solution was weighed into smooth flat-bottom polymethylpentene Petri dishes (nominal 10 cm diameter) to give membranes with nominal 50 and 100 µm dry thicknesses. The dishes were placed on a level drying stage in a 70° C. vacuum oven under nitrogen purge. The dried membranes were freed by soaking in 15% nitric acid followed by a second soaking overnight in fresh 15% nitric acid. The membranes swelled about 5% in diameter and about 20% in weight. The membranes were then soaked in fresh deionized water until the washings were neutral. The membranes were tough, and had swelled about 20% in diameter and about 60% in weight.

Thermal analysis showed a broad melting point with a peak at 102° C. (10 J/g) and an end of melting temperature of 168° C., a crystallization peak at 82° C., and a glass transition temperature of −10° C. The conductivity results are shown below in Table 1 for an in-plane sample with a width of 15.99 mm and a thickness of 120 µm, and a through-plane sample with a thickness of 77 µm.

TABLE 1

| Temperature ° C. | Relative Humidity % | In-Plane Conductivity mS/cm | Through-Plane Conductivity mS/cm |
|---|---|---|---|
| 80 | 95 | 356 | 397 |
| 80 | 50 | 38 | 47 |
| 80 | 25 | 0.2 | 0.5 |

Example 5

The polymerization procedure of Example 4 was repeated to give 2.93 g of polymer (67% yield). $\eta_{inh}$ (0.5 g/dL DMSO) 2.20 dL/g. Gel permeation chromatography in DMAc showed a bimodal molecular weight distribution with a high molecular weight peak: $M_n$ 77,900, $M_w$ 125,000, $M_z$ 207,000.

The polymer was dissolved in DMF (50 mL) with heating to 50° C. The solution was filtered through a glass microfiber filter fitted to a stainless steel filter body using nitrogen pressure and collected in a plastic bottle. Membranes were cast by weighing sufficient solution into square (9 cm×9 cm) smooth flat-bottom glass dishes to give nominally 100 µm dry thicknesses. The dishes were placed on a level drying stage in a cool vacuum oven under nitrogen purge. The dried membranes were heated to 70° C. for 7 hours. The membranes were freed by soaking in 15% nitric acid followed by a second soaking overnight in fresh 15% nitric acid. The membranes were then soaked in fresh deionized water until the washings were neutral. The membranes were tough and had swelled about 60% in weight. The conductivity results are shown below in Table 2 for an in-plane sample with a width of 15.99 mm and a thickness of 105 µm, and a through-plane sample (2 ply) with a thickness of 228 µm.

TABLE 2

| Temperature ° C. | Relative Humidity % | In-Plane Conductivity mS/cm | Through-Plane Conductivity mS/cm |
|---|---|---|---|
| 80 | 95 | 460 | 401 |
| 80 | 50 | 36 | — |
| 80 | 25 | 0.2 | — |

Example 6

Inside the glove box, a 200 mL round-bottom flask equipped with a stirring bar and a septum was charged with bis(1,5-cyclooctadiene)nickel(0) (6.11 g, 22.22 mmol), 1,5-cyclooctadiene (2.40 g, 22.22 mmol), 2,2'-bipyridine (3.48 g, 22.22 mmol), and DMF (50 mL). The flask was stirred for 1 hour to give a dark violet-colored solution. N,N'-bis(4'-bromo-biphenyl-4-sulfonyl)-octafluorobutane-1,4-disulfonamide, disodium salt (10.94 g, 11 mmol) was added to the flask The dark mixture thickened quickly. The flask was heated to 60° C. under nitrogen overnight. The reaction mixture was poured into concentrated hydrochloric acid to precipitate the solid polymer and chopped in a blender to disperse into particles. The polymer was collected by vacuum filtration and washed with hexane. The polymer was dissolved in DMF, filtered, and re-precipitated as before in concentrated hydrochloric acid. The polymer was collected by vacuum filtration and washed with hexane. The polymer was stirred with 15% hydrochloric acid overnight, collected by vacuum filtration, and washed twice with water. The polymer was dried in the vacuum oven at 70° C. under nitrogen purge to give 9.04 g (100% yield) of poly(p-quaterphenylene-sulfonimide-1,4-octafluorobutane-sulfonimide). $\eta_{inh}$ (0.5 g/dL DMSO) 1.74 dL/g. Gel permeation chromatography in DMAc showed a normal molecular weight distribution: $M_n$ 40,000, $M_w$ 83,400, $M_z$ 148,000.

The polymer (3.3 g) was dissolved in DMF (30 mL) with heating to 50° C. The solution was filtered through a glass microfiber filter and a 5 μm PTFE membrane filter fitted to a stainless steel filter body using nitrogen pressure and collected in a plastic bottle. Sufficient solution was weighed into a square (11 cm×11 cm) smooth flat-bottom glass dish and a smooth flat-bottom polymethylpentene Petri dish (nominal 10 cm diameter) to give membranes with nominal 175 μm dry thicknesses. The dishes were dried for several days on a level drying stage inside a nitrogen-purged drying chamber, then overnight at 80° C. in a nitrogen-purged vacuum oven. The dried membranes were freed from the dishes by soaking in 15% nitric acid and washed by soaking in fresh deionized water until the washings were neutral. The membranes were then re-soaked in 15% nitric acid followed by deionized water as before. The membranes were tough. The conductivity results are shown below in Table 3 for an in-plane sample with a thickness of a 112 μm and a width of 15.99 mm, and a through-plane sample with a thickness of 136 μm

TABLE 3

| Temperature ° C. | Relative Humidity % | In-Plane Conductivity mS/cm | Through-Plane Conductivity mS/cm |
|---|---|---|---|
| 80 | 95 | 440 | 214 |
| 80 | 50 | 34 | 47 |
| 80 | 25 | 0.3 | 0.2 |

3-Bromo-Dibenzothiophene-5,5-Dioxide

This compound was synthesized according to the procedure of H. Gilman, A. L. Jacoby, H. A. Pacevitz *Journal of Organic Chemistry* 1938, 3, 120.

A 1 L three-neck round-bottom flask equipped with an addition funnel, mechanical stirrer, and thermocouple was charged with glacial acetic acid (110 mL) and sulfuric acid (110 mL) under nitrogen followed by dibenzothiophene-5,5-dioxide (50 g, 0.231 mol). The slurry was stirred and cooled to below 0° C. Fuming nitric acid, 90% (118 mL, 2.5 mol; specific gravity 1.5) was added dropwise over a period of 1.5 hours to keep the temperature below 4° C. The slurry was stirred for 30 minutes then poured onto 1.5 kg ice rinsing the flask with water. The product was collected by vacuum filtration, washed with water several times, and air dried followed by drying in a vacuum oven. The product was recrystallized from acetonitrile to give 51 g yellow crystals of 3-nitro-dibenzothiophene-5,5-dioxide (85% yield).

A 3 L round-bottom-flask equipped with a stirring bar, reflux condenser, and gas inlet was charged with 3-nitro-dibenzothiophene-5,5-dioxide (26 g, 0.1 mol), n-propanol (280 mL), water (840 mL), concentrated hydrochloric acid (325 mL), and tin powder, 20 mesh (65 g, 0.55 mol) then purged with nitrogen. The slurry was heated to a reflux overnight, which led to the consumption of the yellow crystals. The hot solution was filtered to remove the remaining tin powder then cooled to room temperature and chilled in an ice bath to crystallize the product. The yellow crystals were collected by vacuum filtration without washing with water then air dried. The crystals were added to a 10% solution of sodium hydroxide (200 mL) to liberate the free amine from the hydrochloride salt. The yellow powder was collected by vacuum filtration, washed well with water, then dried under vacuum to give 21.5 g of 3-amino-dibenzothiophene-5,5-dioxide (93% yield).

A 1 L three-neck round-bottom flask equipped with a mechanical stirrer and thermocouple was charged with sulfuric acid (100 mL). Sodium nitrite (15 g, 0.22 mol) was added gradually with vigorous stirring. 3-Amino-dibenzothiophene-5,5-dioxide (20.8 g, 0.090 mol) was dissolved in glacial acetic acid (500 mL) by heating to a near reflux then cooled rapidly in an ice bath to give a fine suspension. The sulfuric acid solution was cooled to 10° C. in an ice bath then the suspension was added gradually to keep the temperature below 20° C. The mixture took on an orange color for the diazonium salt and was stirred for 30 minutes until homogeneous.

A 2 L three-neck round-bottom flask equipped with a mechanical stirrer, stopper, and gas inlet was charged with copper(I) bromide (50 g, 0.31 mol) and concentrated hydrobromic acid (500 mL) then stirred to give a dark solution. The diazonium salt was added gradually and the mixture was stirred for an hour to give a fine granular solid. The product was collected by vacuum filtration and washed well with water to give a light tan solid, which was dried under vacuum. The product was recrystallized from acetonitrile to give 21.5 g of 3-bromo-dibenzothiophene-5,5-dioxide (81% yield).

Example 7

A 200 mL round-bottom flask equipped with a stirring bar, reflux condenser, and gas inlet was charged with 3-bromo-dibenzothiophene-5,5-dioxide (10.36 g, 36 mmol) and chloroform (50 mL) then purged with nitrogen. Chlorosulfonic acid (8 mL, 120 mmol) was added, which dissolved the suspended solids. The solution was heated to a reflux overnight then cooled to room temperature. The excess acid was quenched by adding water (1 mL) dropwise, which caused a solid to separate from solution. The mixture was diluted with hexanes (50 mL). The product was collected by vacuum filtration, washed well with hexanes and water, and dried under vacuum. The product was recrystallized from chloroform to 11.81 g of 7-bromo-dibenzothiophene-5,5-dioxide-3-sulfonyl chloride, shown below (83% yield). $^1$H NMR (CDCl$_3$): 7.78 (d, J=8.3 Hz, 1H), 7.88 (dd, J=8.3 and 1.8 Hz, 1H), 8.02 (d, J=8.3 Hz, 1H), 8.03 (d, J=1.8 Hz, 1H), 8.31 (dd, J=8.3 and 1.8 Hz, 1H), 8.45 (d, J=1.8 Hz, 1H).

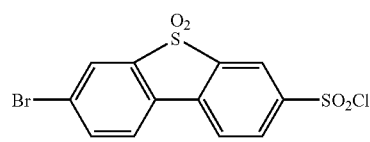

Example 8

Inside the glove box, a 200 mL round-bottom flask equipped with a reflux condenser, stirring bar, and septum was charged with 7-bromo-dibenzothiophene-5,5-dioxide-3-sulfonyl chloride (11.8 g, 30 mmol), octafluorobutane-1,4-disulfonamide (5.40 g, 15 mmol), and acetonitrile (75 mL). Triethylamine (9 mL, 65 mmol) was added slowly by syringe to give a mild exotherm. The solution was heated to a reflux overnight. The solution was cooled to room temperature and poured into an aqueous solution of sodium hydroxide (2.6 g, 0.1 mol) in water (200 mL) in a 1 L round-bottom flask. The solvents were evaporated on a rotary evaporator and the solids were dried under vacuum. The solids were recrystallized by dissolving in water (750 mL) at a reflux, treating with decolorizing carbon, filtering the solution, and concentrating the solution at a reflux to 250 mL to induce crystallization. The white solids were collected by vacuum filtration and dried in the vacuum oven. The recrystallization was repeated twice more from water. The white solids were dried overnight in a vacuum oven at 150° C. under a nitrogen purge to give 10.38 g of N,N'-bis(7-bromo-dibenzothiophene-5,5-dioxide-3-sulfonyl)-octafluorobutane-1,4-disulfonamide, disodium salt, shown below (62% yield). $^1$H NMR (DMSO-$d_6$): 8.06 (dd, J=8.3 and 1.8 Hz, 2H), 8.13 (d, J=1.6 Hz, 2H), 8.15 (dd, J=8.1 and 1.6 Hz, 2H), 8.20 (d, J=8.3 Hz, 2H), 8.36 (d, J=8.1 Hz, 2H), 8.39 (d, J=1.8 Hz, 2H). $^{19}$F NMR (DMSO-$d_6$): −120.38 (m, —CF$_2$—CF$_2$—), −113.06 (m, 2 —CF$_2$—SO$_2$—). −120.35 (m, —CF$_2$—CF$_2$—), −112.97 (m, 2 —CF$_2$—SO$_2$—). $\eta_{inh}$ (0.5 g/dL DMSO) 1.61 dL/g. Gel permeation chromatography in DMAc showed a bimodal molecular weight distribution: $M_n$ 27,500, $M_w$ 83,700, $M_z$ 204,000. Thermo-gravimetric analysis (10° C./min scan rate) showed an onset of decomposition at 265° C. under nitrogen. DSC (10° C./min scan rate) showed a glass transition temperature at 227° C.

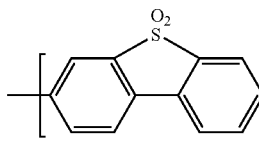 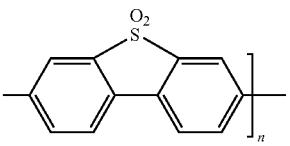

The polymer (4 g) was dissolved in DMF (53 mL) with heating to 50° C. The solution was filtered through a glass microfiber filter fitted to a stainless steel filter body using nitrogen pressure and collected in a flask. Sufficient solution was weighed into two smooth flat-bottom polymethylpentene Petri dishes (nominal 10 cm diameter) to give membranes with nominal 100 μm dry thicknesses. The dishes were dried for two days on a level drying stage in a cool vacuum oven under nitrogen purge. The dried membranes were then heated to 70° C. for 10 hours, which freed the membranes from the dishes. The membranes were soaked in 15% nitric acid followed by a second soaking overnight in fresh 15% nitric acid. The membranes were then soaked in fresh deionized water until the washings were neutral. The membranes were tough and had swelled about 260% in weight. The conductivity

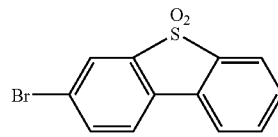 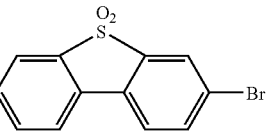

Example 9

Inside the glove box, a 100 mL round-bottom flask equipped with a stirring bar and a septum was charged with bis(1,5-cyclooctadiene)nickel(0) (2.78 g, 10.1 mmol), 1,5-cyclooctadiene (1.09 g, 10.1 mmol), 2,2'-bipyridine (1.58 g, 10.1 mmol), and DMF (25 mL). The flask was stirred for ¾ hour to give a dark violet-colored solution. N,N'-bis(7-bromo-dibenzothiophene-5,5-dioxide-3-sulfonyl)-octafluorobutane-1,4-disulfonamide, disodium salt (5.59 g, 5 mmol) was added to the flask. The dark mixture thickened and had a slight exotherm. The flask was heated to 60° C. under nitrogen for two days. The reaction mixture was poured into concentrated hydrochloric acid to precipitate the solid polymer and chopped in a blender to disperse into particles. The polymer was collected by vacuum filtration and washed with hexane. The polymer was dissolved in DMF, filtered, and re-precipitated as before in concentrated hydrochloric acid. The polymer was collected by vacuum filtration and washed with hexane. The polymer was dried in the vacuum oven at 70° C. under nitrogen purge to give 4.81 g (100% yield) of poly[bis(3,7-dibenzothiophene-5,5-dioxide)-sulfonimide-1,4-octafluorobutane-sulfonimide], shown below. $^1$H NMR (DMSO-$d_6$): 8.15 (bs, 2H), 8.17 (d, 8.0 Hz, 2H), 8.40 (bs, 4H), 8.43 (d, 8 Hz, 2H), 8.67 (bs, 2H). $^{19}$F NMR (DMSO-$d_6$):

results are shown below in Table 4 for an in-plane sample with a thickness of a 112 μm and a width of 11.85 mm, and a through-plane sample with a thickness of 172 μm.

TABLE 4

| Temperature ° C. | Relative Humidity % | In-Plane Conductivity mS/cm | Through-Plane Conductivity mS/cm |
| --- | --- | --- | --- |
| 80 | 95 | 464 | 226 |
| 80 | 50 | 74 | 85 |
| 80 | 25 | 4.6 | 5.2 |

Example 10

Inside the glove box, a 50 mL round-bottom flask equipped with a stirring bar and a septum was charged with bis(1,5-cyclooctadiene)nickel(0) (2.78 g, 10.1 mmol), 1,5-cyclooctadiene (1.09 g, 10.1 mmol), 2,2'-bipyridine (1.58 g, 10.1 mmol), and DMF (30 mL). A 100 mL round-bottom flask equipped with a stirring bar and a septum was charged with N,N'-bis(7-bromo-dibenzothiophene-5,5-dioxide-3-sulfonyl)-octafluorobutane-1,4-disulfonamide, disodium salt (5.59 g, 5 mmol) and DMF (10 mL). The flasks were heated to 60° C. under nitrogen and stirred to dissolve the solids. The catalyst solution was added to the monomer solution by cannula. The dark solution stirred at 60° C. under nitrogen overnight. The reaction mixture was poured into concentrated hydrochloric acid to precipitate the solid polymer and chopped in a blender to disperse into particles. The polymer was collected by vacuum filtration and washed with hexane. The polymer was dissolved in DMF and re-precipitated as before in concentrated hydrochloric acid. The polymer was dissolved in DMF, filtered through a glass microfiber filter, and re-precipitated as before in concentrated hydrochloric acid. After drying overnight, the polymer still weighed much more than the expected amount. The polymer was dissolved in DMF and precipitated in a 1:1 mixture of concentrated hydrochloric acid and hexane. The polymer was collected by vacuum filtration and washed with twice with concentrated hydrochloric acid followed by a 1:1 mixture of concentrated hydrochloric acid and hexane. The polymer was dried in the vacuum oven at 70° C. under nitrogen purge to give 4.21 g (92% yield) of poly[bis(3,7-dibenzothiophene-5,5-dioxide)-sulfonimide-1,4-octafluorobutane-sulfonimide]. $\eta_{inh}$ (0.5 g/dL DMSO) 2.84 dL/g. Gel permeation chromatography in DMAc showed a bimodal molecular weight distribution: $M_n$ 42,800, $M_w$ 150,000, $M_z$ 436,000.

The polymer (4.3 g) was dissolved in DMF (58 mL) with heating to 50° C. The solution was filtered through a glass microfiber filter and a 5 μm PTFE membrane filter fitted to a stainless steel filter body using nitrogen pressure and collected in a plastic bottle. Sufficient solution was weighed into two square (11 cm×11 cm) smooth flat-bottom glass dishes and a smooth flat-bottom polymethylpentene Petri dish (nominal 10 cm diameter) to give membranes with nominal 125 μm dry thicknesses. The dishes were dried for several days on a level drying stage inside a nitrogen-purged drying chamber, then overnight at 100° C. in a nitrogen-purged vacuum oven. The dried membranes were freed from the dishes by soaking in 15% nitric acid and washed by briefly soaking in fresh deionized water until the washings were neutral. The membranes were then re-soaked in 15% nitric acid followed by deionized water as before. The membranes were tough and had swelled about 12-14% in diameter. The conductivity results are shown below in Table 5 for an in-plane sample with a thickness of 104 μm and a width of 15.99 mm, and a through-plane sample with a thickness of 105 μm.

TABLE 5

| Temperature ° C. | Relative Humidity % | In-Plane Conductivity mS/cm | Through-Plane Conductivity mS/cm |
|---|---|---|---|
| 80 | 95 | 383 | 183 |
| 80 | 50 | 44 | 50 |
| 80 | 25 | 3.1 | 4.9 |

Example 11

Inside the glove box, a 100 mL round-bottom flask equipped with a stirring bar and a septum was charged with bis(1,5-cyclooctadiene)nickel(0) (2.78 g, 10.1 mmol), 1,5-cyclooctadiene (1.09 g, 10.1 mmol), 2,2'-bipyridine (1.58 g, 10.1 mmol), and DMF (10 mL). A 100 mL round-bottom flask equipped with a stirring bar and a septum was charged with N,N'-bis(7-bromo-dibenzothiophene-5,5-dioxide-3-sulfonyl)-octafluorobutane-1,4-disulfonamide, disodium salt (5.593 g, 5 mmol), 3,7-dibromo-dibenzothiophene-5,5-dioxide (0.748 g, 2 mmol), and DMF (30 mL). The flasks were heated to 60° C. under nitrogen and stirred to dissolve the solids. The monomer solution was added to the catalyst solution by cannula as quickly as possible. The dark solution was stirred at 60° C. under nitrogen for 15 minutes to give a highly viscous solution. The temperature was increased to 70° C., where the solution again became highly viscous after 2 hours, and stirred overnight. The next day the reaction mass was unstirrable, so it was heated to 95° C. in increments over 2 hours until it could be stirred with some difficulty. The reaction mixture was cooled to room temperature to give a gel. The gel was transferred to a blender containing a 1:1 mixture of hexane and concentrated hydrochloric acid to precipitate the solid polymer and disperse into particles. The polymer was collected by vacuum filtration then washed with hexane and concentrated hydrochloric acid. The polymer was dissolved in DMF and re-precipitated as before in concentrated hydrochloric acid. The polymer was dissolved in DMF (100 mL), filtered to remove a small quantity of gel, re-precipitated as before, and washed twice with concentrated hydrochloric acid. The polymer was dried in the vacuum oven at 80° C. under nitrogen purge to give 4.77 g (81% yield) of poly[oligo (3,7-dibenzothiophene-5,5-dioxide)-sulfonimide-1,4-octafluorobutane-sulfonimide], shown below. $\eta_{inh}$ (0.5 g/dL DMSO) 1.63 dL/g. Gel permeation chromatography in DMAc showed a bimodal molecular weight distribution: $M_n$ 25,300, $M_w$ 85,400, $M_z$ 263,000.

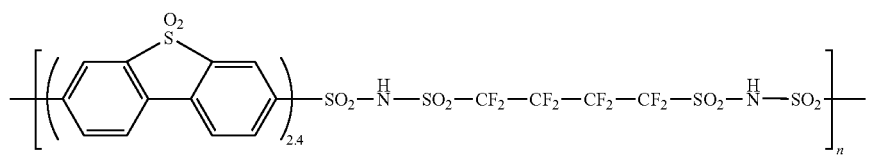

The polymer (4.86 g) was dissolved in DMF (64.5 g) with heating to 50° C. The solution was filtered through a glass microfiber filter and a 5 μm PTFE membrane filter fitted to a stainless steel filter body using nitrogen pressure and collected in a plastic bottle. Sufficient solution (14.16 g) was weighed into a smooth flat-bottom polymethylpentene Petri dish (nominal 10 cm diameter) to give a membrane with a nominal 125 μm dry thickness. The dish was dried for several days on a level drying stage inside a nitrogen-purged drying chamber, then overnight at 100° C. in a nitrogen-purged vacuum oven. The dried membrane had separated from the dish, weighed 1.05 g, and was 9.4 cm in diameter. The membrane was soaked in 15% nitric acid and washed by briefly soaking in fresh deionized water until the washings were neutral. The membrane was then re-soaked in 15% nitric acid followed by deionized water as before. The membrane was tough, and had swelled to 1.52 g (45%) in weight and to 9.9 cm (5.4%) in diameter. The conductivity results are shown below in Table 6 for an in-plane sample with a thickness of 104 μm and a width of 15.99 mm, and a through-plane sample with a thickness of 105 μm. Thermo-gravimetric analysis (10° C./min scan rate) showed an onset of decomposition at 280° C. under nitrogen. DSC (10° C./min scan rate) showed a glass transition temperature at 112° C. with a broad melting point from 125 to 235° C. (2.7 J/g) with a peak at 186° C.

TABLE 6

| Temperature ° C. | Relative Humidity % | In-Plane Conductivity mS/cm | Through-Plane Conductivity mS/cm |
|---|---|---|---|
| 80 | 95 | 383 | 183 |
| 80 | 50 | 44 | 50 |
| 80 | 25 | 3.1 | 4.9 |

Example 12

Inside the glove box, a 100 mL round-bottom flask equipped with a stirring bar and a septum was charged with N,N'-bis(7-bromo-dibenzothiophene-5,5-dioxide-3-sulfonyl)-octafluorobutane-1,4-disulfonamide, disodium salt (5.593 g, 5 mmol), 3,7-dibromo-dibenzothiophene-5,5-dioxide (1.122 g, 3 mmol), and DMF (40 mL). A 50 mL round-bottom flask equipped with a stirring bar and a septum was charged with bis(1,5-cyclooctadiene)nickel(0) (4.45 g, 16.16 mmol), 1,5-cyclooctadiene (1.75 g, 16.16 mmol), 2,2'-bipyridine (2.52 g, 16.16 mmol), and DMF (20 mL). The flasks were heated to 70° C. under nitrogen and stirred to dissolve the solids. The catalyst solution was added dropwise to the monomer solution by cannula. The dark solution was stirred at 70° C. to give a hard gel then kept at temperature overnight. The reaction mass was heated to 100° C. for 1 hour without any change in texture then cooled to room temperature. The gel was transferred to a blender containing concentrated hydrochloric acid to precipitate the solid polymer and disperse into particles. The polymer was collected by vacuum filtration and washed with hexane and concentrated hydrochloric acid. After drying in a vacuum oven at 70° C., the polymer weighed 5.52 g. The polymer was dissolved in DMSO (200 mL), filtered to remove a small quantity of gel, which was washed with DMSO (50 mL), and re-precipitated as before in concentrated hydrochloric acid. The polymer was dried in the vacuum oven at 85° C. under nitrogen purge to give poly[oligo(3,7-dibenzothiophene-5,5-dioxide)-sulfonimide-1,4-octafluorobutane-sulfonimide], shown below. Gel permeation chromatography in DMAc showed a normal molecular weight distribution: $M_n$ 49,900, $M_w$ 161,000, $M_z$ 441,000.

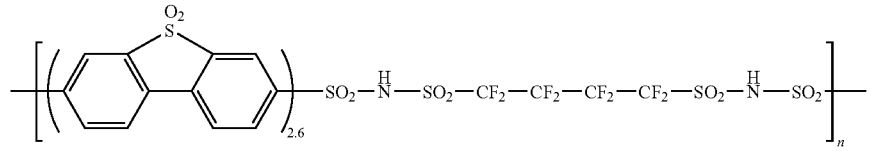

The polymer was dissolved in DMSO (113 g) with heating to 80° C. to give a nominal concentration of 4.3%. The solution was filtered through a glass microfiber filter and a 5 μm PTFE membrane filter fitted to a stainless steel filter body using nitrogen pressure and collected in a plastic bottle. Sufficient solution was weighed into two square (11 cm×11 cm) smooth flat-bottom glass dishes (37.0 g) and two round (nominal 10 cm diameter) smooth flat-bottom polymethylpentene Petri dishes (21.3 g) to give membranes with nominal 130 μm dry thicknesses. The dishes was dried on a level drying stage inside a nitrogen-purged drying chamber, then overnight at 50° C. followed by 100° C. in a nitrogen-purged vacuum oven. The membranes were soaked in 15% nitric acid and washed by briefly soaking in fresh deionized water until the washings were neutral. The membrane was then re-soaked in 15% nitric acid followed by deionized water as before. The membranes were tough. A round sample that was 10.0 cm in diameter weighed 1.158 g. After air drying, it was 8.8 cm in diameter and weighed 0.881 g. After drying at 100° C. inside a nitrogen-purged vacuum oven, the sample had shrunk to 7.7 cm in diameter (30% swell) and to 0.700 g in weight (65 wt % swell). The conductivity results are shown below in Table 7 for an in-plane sample with a thickness of 123 μm and a width of 15.99 mm, and a through-plane sample with a thickness of 123 μm. Thermo-gravimetric analysis (10° C./min scan rate) showed an onset of decomposition at 268-298° C. under nitrogen. DSC (10° C./min scan rate) showed a glass transition temperature at 1° C. with a broad melting point from 50 to 220° C. (8.3 J/g) with a peak at 95° C.

TABLE 7

| Temperature ° C. | Relative Humidity % | In-Plane Conductivity mS/cm | Through-Plane Conductivity mS/cm |
|---|---|---|---|
| 80 | 95 | 310 | 158 |
| 80 | 50 | 32.1 | 33.0 |
| 80 | 25 | 2.3 | 2.7 |

What is claimed is:

1. A process for making a polymer comprising polymerizing a compound of Formula (I):

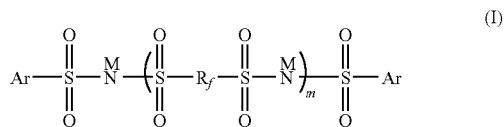

wherein Ar is a univalent group of Formula (II), (III), or (IV):

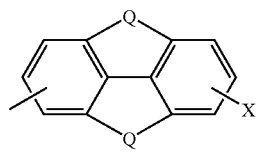

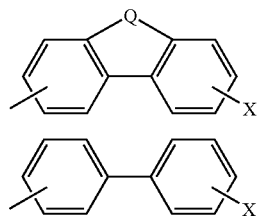

(III)

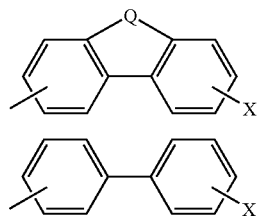

(IV)

and is optionally substituted with one or more fluorine;
  $R_f$ is a straight chain, branched or cyclic, perfluorinated alkylene group having from 1 to 20 carbon atoms and optionally substituted with one or more ether oxygens or halogens;
  m is 1-6;
  M is one or more of monovalent cation;
  Q is S, $SO_2$, CO, or $CR^1R^2$, wherein $R^1$ and $R^2$ are independently branched or cyclic perfluorinated alkyl groups having 1 to 10 carbon atoms, and wherein $R^1$ and $R^2$ can together form a ring; and
  X is chlorine, bromine, iodine, methanesulfonate, or trifluoromethanesulfonate;
  wherein the polymerization is performed in the presence of a zerovalent transition metal and a neutral ligand.

2. The process of claim 1 wherein the zerovalent transition metal is palladium or nickel.

3. The process of claim 1 wherein the zerovalent transition metal is bis(1,5-cyclooctadiene)nickel(0) and the neutral ligand is 2,2'-bipyridine.

4. The process of claim 1 wherein the zerovalent transition metal and neutral ligand are in the form of a complex.

5. The process of claim 1 wherein an accelerator is present.

6. The process of claim 1 wherein the polymerization is performed in a solvent.

7. The process of claim 6 wherein the solvent is one or more of N,N-dimethylformamide, toluene, tetrahydrofuran, acetone, anisole, acetonitrile, N,N-dimethylacetamide, or N-methylpyrrolidinone.

8. The process of claim 1 wherein M is K, Na, Li, or H.

9. The process of claim 1 wherein $R_f$ is a perfluorinated alkylene group having from 2 to 10 carbon atoms.

10. The process of claim 9 wherein $R_f$ is a linear, perfluorinated alkylene group having from 2 to 4 carbon atoms.

11. The process of claim 1 wherein a copolymer is formed by polymerizing a compound of Formula (I) and a compound of Formula (IX):

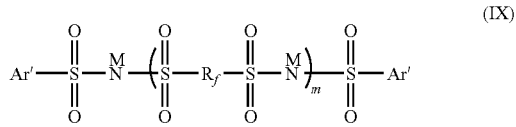

(IX)

wherein Ar' is a univalent group of Formula (X), (XI), or (XII):

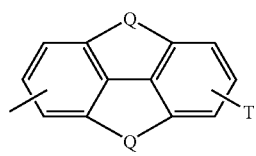

(X)

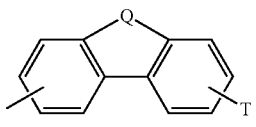

(XI)

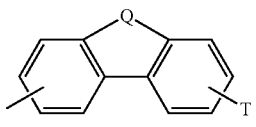

(XII)

wherein T is a boronic acid group or salt thereof, a boronic ester group or a borane group.

12. The process of claim 1 wherein Ar is a univalent group of Formula (VI), (VII), or (VIII):

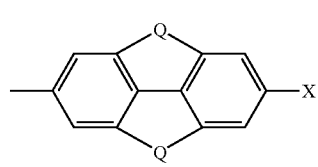

(VI)

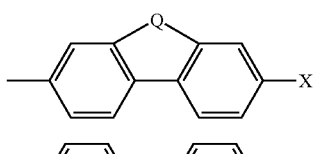

(VII)

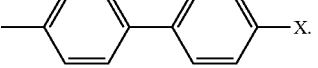

(VIII)

13. The process of claim 12 wherein Ar is Formula (VII) or (VIII).

14. The process of claim 1 wherein m is 1.

15. The process of claim 1 wherein Q is $SO_2$.

16. The process of claim 1 wherein X is Br.

17. A polymer made by the process of claim 1.

18. The polymer of claim 17 that is a homopolymer.

19. The polymer of claim 17 that is a copolymer.

20. A membrane made from the polymer of claim 17.

21. An electrochemical cell comprising the polymer of claim 17.

22. A fuel cell comprising the electrochemical cell of claim 21.

* * * * *